(12) United States Patent
Bollmann et al.

(10) Patent No.: US 6,184,410 B1
(45) Date of Patent: Feb. 6, 2001

(54) CARBODIIMIDES BASED ON 1,3-BIS(1-METHYL-1-ISOCYANATOETHYL)BENZENE

(75) Inventors: Heinz Bollmann, Alfhausen; Karl Häberle, Speyer, both of (DE); Nicolas Kokel, Alleins (FR); Raina Thärigen, Osnabrück (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/298,072

(22) Filed: Apr. 22, 1999

(30) Foreign Application Priority Data

May 14, 1998 (DE) .............................. 198 21 661

(51) Int. Cl.⁷ ..................... C07C 271/20; C07C 275/24; C07C 267/00
(52) U.S. Cl. ......................... 560/26; 521/170; 521/172; 524/195; 528/80; 528/83; 528/84; 528/272; 560/25; 560/27; 560/84; 564/56; 564/252
(58) Field of Search .................. 521/170, 172; 524/195; 528/80, 83, 84, 272; 560/25, 27, 84, 26; 564/56, 252

(56) References Cited

U.S. PATENT DOCUMENTS

| 2,853,473 | 9/1958 | Campbell et al. ............... 260/77.5 |
| 2,941,966 | 6/1960 | Campbell et al. ............... 260/2.5 |
| 3,502,722 | 3/1970 | Neumann et al. ............... 260/566 |
| 5,210,170 | 5/1993 | Quiring et al. ............... 528/80 |
| 5,498,747 | 3/1996 | Pohl et al. ............... 560/25 |
| 5,504,241 | 4/1996 | Pohl et al. ............... 560/25 |
| 5,597,942 | 1/1997 | Pohl et al. ............... 560/25 |
| 5,733,959 | 3/1998 | Heitz et al. ............... 524/1.95 |

FOREIGN PATENT DOCUMENTS

| 1 130 594 | 7/1957 | (DE) . |
| 1 156 401 | 5/1960 | (DE) . |
| 43 18 979 A1 | 12/1994 | (DE) . |
| 44 42 724 A1 | 6/1996 | (DE) . |
| 460 481 A2 | 12/1991 | (EP) . |
| 1 083 410 | 9/1967 | (GB) . |

*Primary Examiner*—Peter O'Sullivan
(74) *Attorney, Agent, or Firm*—Fernando A. Borrego

(57) ABSTRACT

Carbodiimides based on 1,3-bis(1-methyl-1-isocyanatoethyl)benzene contain from 12 to 40% by weight of ethylene oxide units [—$CH_2$—$CH_2$—O—], based on the weight of the carbodiimides.

6 Claims, No Drawings

CARBODIIMIDES BASED ON 1,3-BIS(1-METHYL-1-ISOCYANATOETHYL)BENZENE

The present invention relates to carbodiimides based on 1,3-bis(1-methyl-1-isocyanatoethyl)benzene containing from 12 to 40% by weight of ethylene oxide units [—$CH_2$—$CH_2$—O—], based on the weight of the carbodiimides.

The invention further relates to processes for preparing these carbodiimides and mixtures comprising these carbodiimides and compounds which contain ester structures, preferably polyurethanes containing ester structures.

Organic carbodiimides are known and are used, for example, as stabilizers against hydrolytic degradation of compounds containing ester groups, for example polyaddition and polycondensation products such as polyurethanes. Carbodiimides can be prepared by generally known methods, for example by action of catalysts on monoisocyanates or polyisocyanates with elimination of carbon dioxide. Suitable catalysts are, for example, heterocyclic compounds containing bound phosphorus, e.g. phospholines, phospholenes and phospholidines and also their oxides and sulfides and/or metal carbonyls.

Such carbodiimides, their preparation and use as stabilizers against hydrolytic dissociation of plastics based on polyesters are described, for example, in DE-A 4 318 979, DE-A 4 442 724 and EP-A 460 481.

Particularly for preparing elastomers based on polyurethanes, for example cellular or microcellular polyurethane elastomers, it has been found to be advantageous to mix the carbodiimides as stabilizers into the component comprising water as crosslinker and blowing agent in order to avoid a reaction of acid groups with the carbodiimides.

It is precisely the miscibility of known carbodiimides and thus their incorporation into such an aqueous system which is generally difficult owing to the low solubility.

DE-A 4 318 979 describes the use of 1,3-bis(1-methyl-1-isocyanatoethyl)benzene for preparing carbodiimides and/or oligomeric polycarbodiimides containing terminal isocyanate, urea and/or urethane groups. The terminal isocyanate groups of the carbodiimides described in this document are reacted with customary isocyanate-reactive compounds. Although the carbodiimides described in the examples have, owing to the reaction with polyoxyethylene glycols, a sufficient hydrophilic character due to the very high proportions of ethylene oxide units and are readily miscible with aqueous components, polyurethane elastomers which have been prepared using these carbodiimides display poorer mechanical properties than elastomers which have been prepared without stabilizer. Possible ways of improving these carbodiimides result from the influence of the stabilizers on the dynamic and mechanical properties of, in particular, foamed polyurethane elastomers.

It is an object of the present invention to develop carbodiimides as stabilizers against hydrolytic dissociation of plastics based on polyesters, which carbodiimides can be optimally incorporated into the starting components of the plastics or into the plastics themselves and, in addition, do not have an adverse effect on the dynamic and static properties of the plastics, in particular polyurethane elastomers.

We have found that this object is achieved by carbodiimides based on 1,3-bis(1-methyl-1-isocyanatoethyl)benzene and containing from 12 to 40% by weight, preferably from 15 to 35% by weight, of ethylene oxide units [—$CH_2$—$CH_2$—O—], based on the weight of the carbodiimides.

The preparation of the carbodiimides of the present invention is essentially carried out by means of two reaction steps. On the one hand, (1) carbodiimide structures are generated by the generally known reaction of isocyanate groups with one another to eliminate carbon dioxide in the presence of customary catalysts which are known for this reaction and have been described at the outset, on the other hand, (2) isocyanate groups are reacted with compounds which are reactive toward isocyanates to form urethane and/or urea structures. The order of these two essential process steps (1) and (2) can be as desired, as long as free isocyanate groups are available for the respective reaction.

For example, the carbodiimides of the invention can be obtained by reacting 1,3-bis(1-methyl-1-isocyanatoethyl)benzene in the presence of catalysts with elimination of carbon dioxide to form carbodiimides and subsequently reacting the carbodiimide containing isocyanate groups with at least one compound (i) which is reactive toward isocyanates and comprises ethylene oxide units [—$CH_2$—$CH_2$—O—]. The molar ratio of the NCO groups of the carbodiimide containing isocyanate groups to the groups which are reactive toward isocyanates is usually from 10:1 to 0.2:1, preferably from 5:1 to 0.5:1, particularly preferably from 1:1 to 0.5:1, in particular 1:1.

As an alternative, the carbodiimides of the present invention can be obtained by reacting 1,3-bis(1-methyl-1-isocyanatoethyl)-benzene with at least one compound (i) comprising ethylene oxide units [—$CH_2$—$CH_2$—O—], where the ratio of isocyanate groups used to groups which are reactive toward isocyanates is at least 2:1, and subsequently reacting the reaction product containing isocyanate groups in the presence of catalysts with elimination of carbon dioxide to form carbodiimides.

In this process variant, up to 50% by weight, preferably up to 23% by weight, of the isocyanate groups of the diisocyanate are first reacted with the compounds which are reactive toward isocyanates and the free isocyanate groups are then completely or partially condensed in the presence of catalysts with elimination of carbon dioxide to form carbodiimides and/or oligomeric polycarbodiimides.

Preferably, the reaction to form the carbodiimides is carried out first and the carbodiimide containing isocyanate groups is subsequently reacted with the compounds which are reactive toward isocyanates.

The ethylene oxide units in the carbodiimides are introduced into the carbodiimides via the compounds (i) which are reactive toward isocyanates. For this reason, the isocyanate-reactive compounds (i) which are used according to the present invention in the preparation of the carbodiimides of the present invention are those which contain ethylene oxide units, preferably at least 5 and particularly preferably from 6 to 200 ethylene oxide units, and usually have a number average molecular weight of from 200 to 10,000 g/mol. The ethylene oxide units, which can be represented by the following structure [—$CH_2$—$CH_2$—O—], can be arranged blockwise or distributed in the compound (i). These isocyanate-reactive compounds (i) according to the invention can be prepared, for example, by the generally customary alkoxylation of hydrogen-active initiator substances, for example water, monools, diols, triols, monoamines, diamines and/or triamines usually having molecular weights of from 18 to 500 g/mol, usually in the presence of generally known catalysts, for example alkali metal hydroxides or alkoxides, using alkylene oxides, for example ethylene oxide, propylene oxide and/or butylene oxide, preference being given, according to the present invention, to using ethylene oxide, if desired in admixture with at least one further alkylene oxide. As a result of this method of preparation, for example, these compounds (i)

which are reactive toward isocyanates have hydroxyl groups as reactive groups which react with the isocyanates.

These isocyanate-reactive compounds (i) according to the present invention can, if desired, be used in admixture with further compounds (ii) which are reactive toward isocyanates and have less than 5 or no ethylene oxide units in the preparation of the carbodiimides of the present invention. Possible additional compounds which are reactive toward isocyanates are, for example, compounds which bear at least one, usually from 1 to 3, reactive group(s); suitable reactive groups are, for example, hydroxyl, thiol, primary amino and/or secondary amino groups. These substances which may be used in addition to the isocyanate-reactive compounds (i) according to the present invention usually have molecular weights of from 32 to 500 g/mol. Examples of suitable compounds are compounds which form urethane and/or urea groups by reaction with isocyanates. For example, it is possible to use aromatic, aliphatic and/or araliphatic compounds which have from 1 to 20 carbon atoms and contain hydroxyl and/or amine groups as groups which are reactive toward isocyanates. For example, organic compounds containing at least one hydroxyl group, at least one amine group and/or at least one hydroxyl group and at least one amine group can be used as compounds containing groups which are reactive toward isocyanates. For example, the alcohols mentioned in DE-A 4 318 979 can be used. Furthermore, it is possible to use aromatic, araliphatic and/or aliphatic polyols having from 2 to 20 carbon atoms, for example: 1,2-ethanediol, 1,3-propanediol, 1,2-propanediol, 1,4-, 2,4- and/or 2,3-butanediol, 1,5-pentanediol, 1,6-hexanediol, 1,7-heptanediol, 1,8-octanediol, 1,10-decanediol, neopentyl glycol, 2-methylpropane-1,3-diol, 2- and 3-methylpentane-1,5-diol, the isomers of bis (hydroxymethyl or hydroxyethyl)benzene, hydroxyalkyl ethers of dihydroxybenzenes, trimethylolpropane, glycerol, pentaerythritol and/or sugars containing, for example, 4, 5 or 6 hydroxyl groups.

For the purposes of the present invention, amines are amines containing at least one primary and/or secondary amine group. Examples which may be mentioned are: amines which have a molecular weight of from 31 to 500 g/mol, preferably from 60 to 300 g/mol, and contain at least one primary or secondary amino group. Further examples are diamines such as diaminoethane, diaminopropane, diaminobutane, diaminopentane, diaminohexane, piperazine, 2,5-dimethylpiperazine, 1-amino-3,3,5-trimethyl-5-aminomethylcyclohexane (isophoronediamine, IPDA), 4,4'-diaminodicyclohexylmethane, 1,4-diaminocyclohexane, aminoethylethanolamine, hydrazine, hydrazine hydrate and/or triamines such as diethylenetriamine and/or 1,8-diamino-4-aminomethyloctane.

It is also possible to use amines which are derived from the amines mentioned by substitution of one or more primary amine groups by further substituents such as alkyl groups to give secondary amine groups. Furthermore, compounds which have both at least one hydroxyl group and at least one amine group can also be used, for example ethanolamine, propanolamine, isopropanolamine, aminoethylethanolamine or N-alkylamines derived therefrom.

Suitable alcohols and amines are mentioned, for example, in DE-A 4 318 979, page 4, lines 29 to 33.

Preference is given to using the isocyanate-reactive compounds (i) according to the present invention together with monofunctional compounds in order to regulate the molecular weight of the carbodiimides of the present invention, particularly if the diisocyanates are converted into the carbodiimides in a first step and the reaction of the carbodiimides containing isocyanate groups with the compounds which are reactive toward isocyanates is carried out subsequently. As monofunctional compounds which are reactive toward isocyanates, it is possible to use, for example, amines and preferably alcohols. Suitable amines, e.g. primary or preferably secondary amines, advantageously have from 1 to 12 carbon atoms, preferably from 2 to 8 carbon atoms. Examples which may be mentioned are methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine and ethylhexylamine and also cyclohexylamine and benzylamine. However, preference is given to using alcohols, e.g. primary or secondary alcohols having from 1 to 18 carbon atoms, preferably from 2 to 8 carbon atoms, for the reaction with the isocyanate groups. Examples of primary or secondary alcohols are: methanol, ethanol, n-propanol, isopropanol, n-butanol, sec-butanol, n-pentanol, industrial pentanol mixtures, n-hexanol, industrial hexanol mixtures, 2-ethylhexanol, octanol, 2-ethyloctanol, decanol and dodecanol and also cyclohexanol and benzyl alcohol.

Alkoxylation products such as the compounds (i) are also preferred, but with the proviso that they contain less than 5 EO units. Such alkoxylation products do not contribute to the hydrophilicity of the carbodiimides of the present invention; they are therefore not taken into account in the calculation of the EO content. Examples which may be mentioned here are monoalkyl ethers of mono-, di-, tri- and tetraethylene glycol such as diethylene glycol monobutyl ether or diethylene glycol monoethyl ether.

As compounds which are reactive toward isocyanates for preparing the carbodiimides of the present invention, particular preference is given to using a mixture comprising:
(i) compounds which are reactive toward isocyanates and contain at least 5 ethylene oxide units and have already been described at the outset and
(ii) compounds which are reactive toward isocyanates and contain no or less than 5 ethylene oxide units, preferably at least one monoalcohol and/or monoamine, particularly preferably at least one monoalcohol.

In the reaction of the isocyanate groups with the compounds which are reactive toward isocyanates, the compound (i) which is reactive toward isocyanates is preferably used in a substoichiometric amount based on the isocyanate groups, particularly preferably at a ratio of NCO groups to the groups which are reactive toward isocyanates of from 1:0.1 to 1:0.9. Remaining isocyanate groups are preferably converted by means of the monools. However, isocyanate groups of the carbodiimide can also be retained. The molar ratio of (i):(ii) is preferably from 0.1:1 to 9:1.

In the preparation of the carbodiimides of the present invention, the type of compounds which are reactive toward isocyanates, for example the ratio of (i) to (ii), has to be selected in each case so as to ensure that the process products according to the present invention, viz. the carbodiimides, contain from 12 to 40% by weight of ethylene oxide units, based on the total weight of the carbodiimides.

The process step (1) for preparing the carbodiimides of the present invention by reaction of diisocyanates with elimination of carbon dioxide can be carried out at elevated temperatures, e.g. at from 50 to 200° C., preferably from 150 to 185° C., advantageously in the presence of catalysts. Methods suitable for this purpose are described, for example, in GB-A-1 083 410, DE-A 1 130 594 and DE-A-11 56 401. Catalysts which have been found to be particularly useful are, for example, phosphorus compounds which are preferably selected from the group consisting of phospholenes, phospholene oxides, phospholidines and phospholine oxides. When the reaction mixture has the desired content of NCO groups, the polycarbodiimide formation is usually stopped. This can be achieved by distilling off the catalysts under reduced pressure or by deactivating them by addition of a deactivator, e.g. phosphorus trichloride. The polycarbodiimide preparation can, furthermore, be carried out in the absence or presence of solvents which are inert under the reaction conditions.

A person skilled in the art can set the degree of condensation in the customary way by appropriate selection of the reaction conditions, e.g. the reaction temperature, the type and amount of catalyst and the reaction time. The course of the reaction can be followed most simply by determining the NCO content. Other parameters such as increase in viscosity, deepening of color or $CO_2$ evolution can also be employed for following and controlling the reaction.

As diisocyanate for preparing the carbodiimides of the present invention, use is made of 1,3-bis(1-methyl-1-isocyanatoethyl)benzene, hereinafter also referred to as TMXDI. The TMXDI can be used in mixtures with further, generally customary isocyanates, for example hexamethylene diisocyanate, 1-isocyanato-3,3,5-trimethyl-5-isocyanatomethylcyclohexane (isophorone diisocyanate), di(cyclohexyl)methane diisocyanate, trimethylhexamethylene diisocyanate, dodecane diisocyanate, octane diisocyanate and/or cyclohexane 1,4-diisocyanate. In this case, preference is given to using at least 30 mol % of TMXDI in the mixture. The carbodiimides of the present invention thus comprise at least one of the following structural units which represents the carbodiimide structure of the diisocyanate according to the present invention:

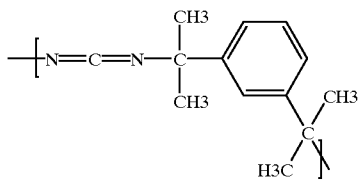

For example, the carbodiimides of the present invention can have the following structure:

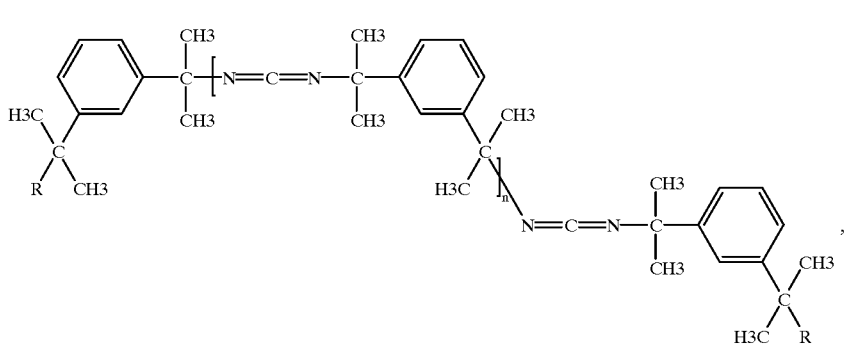

where
R are identical or different, for example —NHCONHR[1]— or —NHCOOR[1]— radicals, where $R^1$ and $R^2$ are derived from the isocyanate-reactive compounds which have already been described above by way of example in the form of the compounds (i) and (ii) and can connect the structure shown to further carbodiimide structures, n is, for example, 0, 1, 2, 3, 4, 5, 6, 7, 8, 9, 10, where n can be an integer as indicated or can, as a statistical average, be a fraction.

The carbodiimides of the present invention comprise at least one, preferably from 1 to 20, carbodiimide structure(s); the mean degree of condensation (number average), i.e. the mean number of carbodiimide structures in the carbodiimides of the present invention, is particularly preferably from 1 to 10. In addition, the compounds of the invention further comprise urethane and/or urea structures which are formed by reaction of isocyanate groups of the diisocyanates used in the preparation with compounds which are reactive toward isocyanates.

The carbodiimide structures of the compounds of the present invention are bound to non-aromatic carbon atoms. This offers the significant advantage that no aromatic amines are liberated on cleavage of the carbodiimides and the carbodiimides of the present invention are therefore of less toxicological concern than the carbodiimides described, for example, in EP-A 460 481.

In the reaction with carboxylic acids and/or carboxyl-containing compounds, the carbodiimides of the present invention based on TMXDI form araliphatic isocyanates having a lower reactivity than aromatic isocyanates. The araliphatic isocyanates formed therefore have virtually no influence on, for example, the index of a polyaddition reaction to form urethane. As a result, the molecular weight of the polyurethanes formed and thus their mechanical properties are constant and very reproducible.

The carbodiimides of the present invention display a high hydrolysis inhibition action and light stability which are at least comparable to those of the industrially used aromatic carbodiimides and aromatic polycarbodiimides and can, with observance of occupational hygiene regulations, be introduced without problems into the polycondensation and polyaddition products containing ester groups. The carbodiimides have good compatibility with the polyaddition and polycondensation products containing ester groups, in particular with polyester urethane rubbers, and can also be homogeneously mixed with these materials in the melt without problems.

The monocarbodiimides and/or oligomeric polycarbodiimides of the present invention are very suitable as acceptor for carboxyl compounds and are therefore preferably used as stabilizers against hydrolytic degradation of compounds containing ester groups, for example polymers containing ester groups, e.g. polycondensation products such as thermoplastic polyesters such as polyethylene terephthalate and polybutylene terephthalate, polyether esters, polyamides, polyesteramides, polycaprolactones and also unsaturated polyester resins and polyester esters, e.g. block copolymers of polyethylene terephthalate or polybutylene terephthalate and polycaprolactone, and polyaddition products, e.g. polyurethanes, polyureas and polyurethane-polyurea elastomers containing ester groups. These compounds containing ester groups are generally known. Their starting materials, methods of preparation, structures and properties are widely described in the standard literature. Owing to their good solubility in the formative components for preparing polyurethanes and their good compatibility with the polyurethanes formed, the (poly)carbodiimides of the present invention are particularly suitable as stabilizers against hydrolytic degradation of polyurethanes, preferably compact or cellular polyurethane elastomers and in particular thermoplastic polyurethanes, and also cellulose or compact elastomers.

If the carbodiimides of the present invention have terminal isocyanate groups, for example if a carbodiimide containing isocyanate groups is used with a substoichiometric amount of groups which are reactive toward isocyanates, the carbodiimides can be used in the preparation of polyaddition products by reaction of isocyanates with compounds which are reactive toward isocyanates. Furthermore, the carbodiimides of the present invention can be used as stabilizers for plastics comprising customary polyamides, polyoxymethylene homopolymers or copolymers which are known to those skilled in the art and are described in the literature.

Furthermore, the carbodiimides of the present invention can be used as crosslinkers in or for aqueous latices. Aqueous latices are described, for example, in DE-A 3 512 918, EP-A 548815, EP-A 582 983 and EP-A 686 626.

The concentration of the carbodiimides of the present invention in the ester-containing polycondensation or polyaddition products to be stabilized is generally from 0.05 to 10% by weight, preferably from 0.1 to 5% by weight, based on the total weight of the mixture. In individual cases, depending on the hydrolytic stress to which the plastic is subjected, the concentration can also be higher.

The carbodiimides which can be used according to the present invention can also be introduced into the ester-containing products to be stabilized by various methods. For example, the carbodiimides of the present invention can be mixed with one of the formative components for preparing the polyaddition products, e.g. the polyisocyanates or/and polyhydroxyl compounds for preparing polyurethanes, or the carbodiimides can be added to the reaction mixture for preparing the polyurethanes. In another process variant, the carbodiimides of the present invention can be incorporated into the melt of the fully reacted polyaddition or polycondensation products. However, it is also possible to coat granulated polyaddition or polycondensation products with the carbodiimides of the present invention or to mix them with pulverized, pelletized or granulated carbodiimides of the present invention and to introduce them into the polymer compositions in a subsequent production of moldings by melt extrusion. To prepare pourable polyurethane elastomers and TPUs based on polyesters, the carboxyl-containing polyester polyols are, according to a preferred embodiment, first treated with the carbodiimides of the present invention to reduce the acid content and are then, if desired with addition of further amounts of carbodiimides, reacted with polyisocyanates, if desired in the presence of additional auxiliaries and additives. Furthermore, the carbodiimides of the present invention can be introduced into the polyurethane via the isocyanate component. However, it is particularly advantageous to introduce the carbodiimides of the present invention into the polymer containing ester groups during conventional processing.

The carbodiimides of the present invention are particularly preferably used in the preparation of polyurethanes, e.g. cellular, for example microcellular, polyurethanes, in particular polyurethane elastomers. These polyurethanes, in particular polyurethane elastomers, can be prepared by the known reaction of customary starting components, i.e. isocyanates, compounds which are reactive toward isocyanates, blowing agents, preferably water, and, if desired, catalysts, auxiliaries and/or additives in the presence of the carbodiimides of the present invention. Here, the carbodiimide of the present invention is preferably added to the component containing the blowing agent, preferably water.

As starting components for preparing the polyurethanes, in particular the polyurethane elastomers, it is possible to use, for example, the following compounds:

As isocyanates, it is possible to use generally customary isocyanates, preferably organic diisocyanates. Specific examples are: alkylene diisocyanates having from 4 to 12 carbon atoms in the alkylene radical, for example dodecane 1,12-diisocyanate, 2-ethyl tetramethylene 1,4-diisocyanate, 2-methyl pentamethylene 1,5-diisocyanate, tetramethylene 1,4-diisocyanate, lysine ester diisocyanate (LDI) and/or hexamethylene 1,6-diisocyanate (HDI); cycloaliphatic diisocyanates such as cyclohexane 1,3- and 1,4-diisocyanate and also any mixtures of these isomers, hexahydrotolylene 2,4- and 2,6-diisocyanate and also the corresponding isomer mixtures, dicyclohexylmethane 4,4'-, 2,2'- and 2,4'-diisocyanate and also the corresponding isomer mixtures and/or 1-isocyanato-3,3,5-trimethyl-5-isocyanatomethylcyclohexane (IPDI). Further possible isocyanates are aromatic diisocyanates and polyisocyanates such as tolylene 2,4- and 2,6-diisocyanate and the corresponding isomer mixtures, diphenylmethane 4,4'-, 2,4'- and 2,2'-diisocyanate and the corresponding isomer mixtures, naphthylene diisocyanate, polyphenylpolymethylene polyisocyanates, mixtures of diphenylmethane 4,4'-, 2,4'- and 2,2'-diisocyanates and polyphenylpolymethylene polyisocyanates (crude MDI) and mixtures of crude MDI and tolylene diisocyanates. Furthermore, diisocyanates and/or polyisocyanates containing ester, urea, allophanate, isocyanurate, biuret, uretdione and/or urethane groups can be used in the process of the present invention.

The isocyanates can be used singly or in mixtures.

As compounds which are reactive toward isocyanates, it is possible to use generally known compounds which have a usual molecular weight of from 60 to 10,000 and contain at least one, preferably from 2 to 6, group(s) which is/are reactive toward isocyanates, for example hydroxyl, thiol and/or amino groups. Examples of compounds which have been found to be useful are polyols selected from the group consisting of polyether polyols, polyester polyols, polythioether polyols, hydroxyl-containing polyacetals and hydroxyl-containing aliphatic polycarbonates or mixtures of at least two of the polyols mentioned. Preference is given to using polyester polyols and/or polyether polyols, preferably polyether polyols and polyester polyols.

Examples of polyether polyols are: polytetrahydrofuran, polyether polyols which can be prepared by customary addition of alkylene oxides onto initiator molecules, preferably adding on ethylene oxide at the end so as to produce primary hydroxyl groups in the polyether polyols as a result of the terminal ethylene oxide units. The polyether polyalcohols preferably have a molecular weight of from 450 to 8000. Suitable polyester polyols can be prepared, for example, from organic dicarboxylic acids having from 2 to 12 carbon atoms, preferably aliphatic dicarboxylic acids having from 4 to 6 carbon atoms, and polyhydric alcohols, preferably diols, having from 2 to 12 carbon atoms, preferably from 2 to 6 carbon atoms. Examples of suitable dicarboxylic acids are: succinic acid, glutaric acid, adipic acid, suberic acid, azelaic acid, sebacic acid, decanedicarboxylic acid, maleic acid, fumaric acid, phthalic acid, isophthalic acid and terephthalic acid. The dicarboxylic acids can be used either individually or in admixture with one another. In place of the free dicarboxylic acids, it is also possible to use the corresponding dicarboxylic acid derivatives such as dicarboxylic esters of alcohols having from 1 to 4 carbon atoms or dicarboxylic anhydrides. Preference is given to using dicarboxylic acid mixtures of succinic, glutaric and adipic acids in weight ratios of, for example, 20-35:35-50:20-32, and in particular adipic acid. Examples of dihydric and polyhydric alcohols, in particular diols, are: ethanediol, diethylene glycol, 1,2- or 1,3-propanediol, dipropylene glycol, 1,4-butanediol, 1,5-pentanediol, 1,6-hexanediol, 1,10-decanediol, neopentyl glycol, glycerol and trimethylolpropane. Preference is given to using ethanediol, diethylene glycol, 1,4-butanediol, 1,5-pentanediol, 1,6-hexanediol, neopentyl glycol or mixtures of at least two of the diols mentioned, in particular mixtures of 1,4-butanediol, 1,5-pentanediol and/or 1,6-hexanediol. It is also possible to use polyester polyols derived from lactones, e.g. $\epsilon$-caprolactone, or hydroxycarboxylic acids, e.g. $\omega$-hydroxycaproic acid.

The polyester polyols preferably have a functionality of from 2 to 4, in particular from 2 to 3, and a molecular weight of from 480 to 4000, preferably from 600 to 3000 and in particular from 600 to 2500.

As compounds which are reactive toward isocyanates, diols and/or triols having molecular weights of from 62 to 400 can be used, if desired, in the process of the present invention as chain extenders and/or crosslinkers. The addition of chain extenders, crosslinkers or, if desired, mixtures thereof can, however, prove to be advantageous for modifying the mechanical properties, e.g. the hardness. The chain extenders and/or crosslinkers preferably have a molecular weight of from 62 to 300. Suitable chain extenders/crosslinkers are, for example, aliphatic, cycloaliphatic and/or aralphatic diols having from 2 to 14, preferably from 4 to 10, carbon atoms, e.g. ethylene glycol, 1,2- and 1,3-propanediol, 1,10-decanediol, 1,2-, 1,3- and 1,4-dihydroxycyclohexane, diethylene glycol, dipropylene glycol and preferably 1,4-butanediol, 1,6-hexanediol and bis(2-hydroxyethyl)hydroquinone, triols such as 1,2,4- or 1,3,5-trihydroxycyclohexane, glycerol and trimethylolpropane and low molecular weight hydroxyl-containing polyalkylene oxides based on ethylene oxide and/or 1,2-propylene oxide and the abovementioned diols and/or triols as initiator molecules.

If chain extenders, crosslinkers, for example water, or mixtures thereof are employed for preparing the polyurethane foams, they are advantageously used in an amount of from 0 to 20% by weight, preferably from 2 to 8% by weight, based on the weight of all the isocyanate-reactive compounds used.

Blowing agents used can be chemically and/or physically acting blowing agents. Suitable physically acting blowing agents are liquids which are inert toward the modified or unmodified polyisocyanates and have boiling points at atmospheric pressure below 100° C., preferably below 50° C., in particular from −50° C. to 30° C., so that they vaporize under the action of the exothermic polyaddition reaction. Examples of such liquids which are preferably used are alkanes such as heptane, hexane, n- and iso-pentane, preferably industrial mixtures of n- and iso-pentanes, n- and iso-butane and propane, cycloalkanes such as cyclopentane and/or cyclohexane, ethers such as furan, dimethyl ether and diethyl ether, ketones such as acetone and methyl ethyl ketone, alkyl carboxylates such as methyl formate, dimethyl oxalate and ethyl acetate and halogenated hydrocarbons such as customary fluorinated hydrocarbons and/or chlorinated hydrocarbons, for example dichloromethane. Mixtures of these low-boiling liquids with one another and/or with other substituted or unsubstituted hydrocarbons can also be used. As chemically acting blowing agent, preference is given to using water which reacts with isocyanate groups to form carbon dioxide. Particular preference is given to using water, if desired in combination with further blowing agents. Also suitable are organic carboxylic acids such as formic acid, acetic acid, oxalic acid, ricinoleic acid and carboxyl-containing compounds.

The amount of physically acting blowing agent used is preferably from 0.5 to 25% by weight, particularly preferably from 3 to 15% by weight, in each case based on the weight of all the isocyanate-reactive compounds used.

The water is preferably added as crosslinker component to a prepolymer.

As catalysts, it is possible to use generally known compounds which strongly accelerate the reaction of the isocyanate groups with the groups which are reactive toward isocyanates. Preference is given to using a total catalyst content of from 0.001 to 15% by weight, in particular from 0.05 to 6% by weight, based on the weight of all the isocyanate-reactive compounds used, for example the following compounds: triethylamine, tributylamine, dimethylbenzylamine, dicyclohexylmethylamine, dimethylcyclohexylamine, bis(N,N-dimethylaminoethyl) ether, bis(dimethylaminopropyl)urea, N-methylmorpholine or N-ethylmorpholine, N-cyclohexylmorpholine, N,N,N',N'-tetramethylethylenediamine, N,N,N',N'-tetramethylbutanediamine, N,N,N',N'-tetramethylhexane-1,6-diamine, pentamethyldiethylenetriamine, dimethylpiperazine, N-dimethylaminoethylpiperidine, 1,2-dimethylimidazole, 1-azabicyclo[2.2.0]octane, 1,4-diazabicyclo[2.2.2]octane (Dabco) and alkanolamine compounds such as triethanolamine, triisopropanolamine, N-methyldiethanolamine and N-ethyldiethanolamine, dimethylaminoethanol, 2-(N,N-dimethylaminoethoxy) ethanol, N,N',N"-tris(dialkylaminoalkyl) hexahydrotriazines, e.g. N,N',N"-tris(dimethylaminopropyl)-s-hexahydrotriazine, triethylenediamine, pentamethyldiethylenetriamine and/or bis(dimethylamino) ether, iron(II) chloride, zinc chloride, lead octoate, tin dioctoate, tin diethylhexanoate, dibutyltin dilaurate and/or dibutyl dilauryl tin mercaptide, 2,3-dimethyl-3,4,5,6-tetrahydropyrimidine, tetraalkylammonium hydroxides such as tetramethylammonium hydroxide, alkali metal hydroxides such as sodium hydroxide and alkali metal alkoxides such as sodium methoxide and potassium isopropoxide, and also alkali metal salts of long-chain fatty acids having from 10 to 20 carbon atoms and possibly lateral OH groups.

Examples of auxiliaries and/or additives are: surface-active substances, foam stabilizers, cell regulators, fillers, dyes, pigments, flame retardants, fungistatic and bacteriostatic substances.

To prepare the polyurethanes, in particular the polyurethane elastomers, the isocyanates and the compounds which are reactive toward isocyanates are reacted in the presence of the carbodiimides of the present invention in such amounts that the equivalence ratio of NCO groups of the isocyanates to the sum of the reactive hydrogen atoms of the compounds which are reactive toward isocyanates is 0.85–1.25:1, preferably 0.95–1.15:1 and in particular 1–1.05:1. If the polyurethanes contain at least some bound isocyanurate groups, use is usually made of a ratio of NCO groups to the sum of reactive hydrogen atoms of 1.5–60:1, preferably 1.5–8:1.

Under the definition employed in this document, compounds or groups which are reactive toward isocyanates do not include isocyanates or isocyanate groups. The carbodiimides of the present invention are, insofar as they contain isocyanate groups or groups which are reactive toward isocyanates, to be included in the above calculation.

The polyurethanes are advantageously prepared by the one-shot method or the prepolymer method, for example by means of the high-pressure or low-pressure technique in open or closed molds, for example metal molds. The continuous application of the reaction mixture to suitable conveyor belts for producing panels is also customary.

It has been found to be particularly advantageous to employ the two-component method and to combine the compounds which are reactive toward isocyanates, the blowing agent or blowing agents and, if used, the catalysts, auxiliaries and/or additives as component (A) and to use the isocyanates or mixtures of the isocyanates and, if desired, blowing agents as component (B).

The carbodiimides of the present invention are preferably incorporated into the component A, particularly preferably into the chain extenders and/or crosslinkers which may be present therein.

It is precisely when used as stabilizers in polyurethane elastomers that the carbodiimides of the present invention display their significant advantages compared to the known carbodiimides. In particular, the stabilizers of the present invention have no adverse effect on the static and dynamic properties of the polyurethane elastomers. Owing to their ethylene oxide content, the carbodiimides of the present invention are very readily incorporated into aqueous components; in addition, the polyurethane elastomers prepared according to the present invention have significantly improved properties compared to elastomers prepared using known carbodiimides, e.g. those known from DE-A 43 18 979.

Apart from their effectiveness as stabilizers against hydrolytic degradation of polyaddition or polycondensation products containing ester groups or for deacidifying polyesterols which can be used for preparing polyester-containing plastics, in particular polyurethane rubbers, the carbodiimides are also suitable, for example, for stopping esterification reactions in the preparation of polyesters when the desired degree of polycondensation has been reached.

EXAMPLES 750 parts by weight (3.1 mol) of 1,3-bis(1-methyl-1-isocyanatoethyl)benzene having an NCO content of 34.4% by weight were heated to 180° C. in the presence of 1.5 parts by weight, based on the isocyanate, of 1-methyl-2-phospholene 1-oxide and in the absence of solvent and condensed at this temperature with moderate evolution of carbon dioxide. After the NCO content of the reaction mixture had reached about 11% by weight, the catalyst which had been added and remaining unreacted 1,3-bis(1-methyl-1-isocyanatoethyl)benzene were distilled off at 180° C. under a pressure of 1 mbar.

Three different batches each gave 570 parts by weight of a mixture of carbodiimides having an NCO content of

| CDI 1: | 8.0% |
| CDI 2: | 10.9% and |
| CDI 3: | 7.9%, | a content of —N=C=N— groups of about 15% by weight (calculated), a melting point of <30° C. and an iodine color number of 5–7 measured in accordance with DIN 6162.

A) Preparation of the carbodiimides

Subsequently, the carbodiimides (CDI) 1, 2 or 3 were reacted at 140° C. in a stirred flask with the alcohols indicated in Table 1 until an NCO content of <0.2% by weight had been reached.

As compound (i), use was made of a methoxypolyoxyethylene alcohol having a number average molecular weight of 520 g/mol and a content of EO units of 94.0% by weight.

The compounds (ii) used are indicated in Table 1.

The batches were calculated such that Σ(A+B)/NCO was always 1.

TABLE 1

| Example | NCO content of carbodiimide (% by weight) | Mass of MPG (g) | Number of moles of MPG (mol) | B | Mass of B (g) | Number of moles of B (mol) | EO content from MPG (% by weight) |
|---|---|---|---|---|---|---|---|
| 1 (Comparison) | 8.0 | ./. | ./. | DEGMBE | 154.5 | 0.952 | ./. |
| 2 (Comparison) | 8.0 | ./. | ./. | DEGMEE | 127.8 | 0.952 | ./. |
| 3 (Comparison) | 8.0 | 495.2 | 0.952 | ./. | ./. | ./. | 46.8 |
| 4 | 8.0 | 240.6 | 0.476 | EH | 62.0 | 0.476 | 28.2 |
| 5 | 8.0 | 165.1 | 0.317 | EH | 82.7 | 0.635 | 21.2 |
| 6 | 8.0 | 123.8 | 0.238 | EH | 93.0 | 0.714 | 16.6 |
| 7 | 10.9 | 337.4 | 0.649 | DEGMEE | 87.1 | 0.649 | 35.0 |
| 8 | 10.9 | 224.9 | 0.433 | DEGMEE | 116.1 | 0.865 | 25.7 |
| 9 | 10.9 | 168.7 | 0.325 | DEGMEE | 130.6 | 0.974 | 20.3 |
| 10 | 10.9 | 126.4 | 0.243 | DEGMEE | 141.4 | 1.054 | 15.8 |
| 11 | 10.9 | 94.3 | 0.181 | DEGMEE | 149.8 | 1.116 | 12.2 |
| 12 | 7.9 | 240.8 | 0.463 | DEGMEE | 64.1 | 0.477 | 28.7 |
| 13 | 7.9 | 190.3 | 0.366 | DEGMEE | 77.8 | 0.574 | 23.8 |
| 14 | 7.9 | 171.6 | 0.330 | DEGMEE | 81.9 | 0.610 | 21.9 |
| 15 | 7.9 | 208.0 | 0.400 | DEGMEE | 72.5 | 0.540 | 25.6 |

DEGMBE: Diethylene glycol monobutyl ether, DEGMEE: Diethylene glycol monoethyl ether, EH: 2-ethylhexanol B) Prepatationof Pur elastomers To prepare PUR elastomers, a prepolymer was prepared from 1000 parts by weight of ethylene glycol adipate (hydroxyl number=56) and 380 g of 4,4'-MDI.

The crosslinker component having a water content of 37.3% was prepared from the above-described carbodiimides and ethoxylates of ricinoleic and oleic acids as foam stabilizers.

The amount of carbodiimide was selected such that the finished PU elastomers contained 0.8% by weight of the respective carbodiimide.

The crosslinker component prepared in this way was added while stirring vigorously to the prepolymer which had been cooled to 90° C. The equivalence ratio of NCO/OH was 1.07.

After stirring for a total of 8 seconds, the reaction mixture was poured into a closable mold heated to 90° C. and was cured for 25 minutes. The mold was configured so as to give a cylindrical test spring having three segment constrictions and a height of 100 mm, an external diameter of 50 mm and an internal diameter of 10 mm. After removal from the mold, the spring was subjected to thermal after-curing at 110° C. for 16 hours.

To test the dynamic mechanical properties, the springs were subjected to 100,000 loading cycles at a force of 6 kN and a frequency of 1.2 Hz. The consolidation CON was determined using the equation $$CON=(H_o-H_r)*100/H_o$$

$H_o$ is the height of the spring before commencement of the test; $H_r$ is the height of the spring after the test, measured after storage for 24 hours at 23° C./50% relative humidity.

The springs were examined visually after the test. The entry "after <number> ex" means that the spring was destroyed after <number> loading cycles. "OK" means "in a satisfactory condition". Two springs/formulation were tested in each case.

The properties measured are shown in Table 2.

TABLE 2

| Example | Carbodiimide from Example | Consolidation | Condition of the springs after 100,000 loading cycles |
|---|---|---|---|
| 16 a | 3 (Comparison) | ./. | after 50,000 ex |
| 16 b | 3 (Comparison) | 24.1 | crack |
| 17 a | 1 (Comparison) | ./. | after 79,000 ex |
| 17 b | 1 (Comparison) | 15 | crack |
| 18 a | 2 (Comparison) | ./. | after 45,000 ex |
| 18 b | 2 (Comparison) | ./. | after 55,000 ex |
| 19 a | 4 | 14.8 | OK |
| 19 b | 4 | 18.3 | crack |
| 20 a | 5 | 18.3 | OK |
| 20 b | 5 | 13.2 | OK |
| 21 a | 6 | 15.1 | OK |
| 21 b | 6 | 15.5 | OK |
| 22 a | 7 | 14.9 | OK |
| 22 b | 7 | 14.7 | OK |
| 23 a | 8 | 14.9 | OK |
| 23 b | 8 | 15.9 | OK |
| 24 a | 9 | 12.3 | OK |
| 24 b | 9 | 12.9 | OK |
| 25 a | 10 | 15.3 | OK |
| 25 b | 10 | 17.3 | OK |
| 26 a | 11 | 16.9 | OK |
| 26 b | 11 | 16.6 | OK |
| 27 a | 12 | 17.6 | OK |
| 27 b | 12 | 18.2 | OK |
| 28 a | 13 | 12.5 | OK |
| 28 b | 13 | 13.0 | OK |
| 29 a | 14 | 12.8 | OK |
| 29 b | 14 | 12.8 | OK |
| 30 a | 15 | 14.1 | OK |
| 30 b | 15 | 13.8 | OK |
| 31 a | 16 | 13.7 | OK |
| 31 b | 16 | 14.0 | OK |

These measured results clearly show that the carbodiimides of the present invention lead, particularly when used as stabilizers in polyurethane elastomers, to products having significantly improved properties.

We claim:

1. A process for preparing carbodiimides based on 1,3-bis(1-methyl-1-isocyanatoethyl)benzene containing from 12 to 40% by weight of ethylene oxide units, based on the weight of the carbodiimides, which comprises reacting 1,3-bis(1-methyl-1-isocyanatoethyl)benzene in the presence of catalysts with elimination of carbon dioxide to form carbodiimides containing isocyanate groups and subsequently reacting said carbodiimides containing isocyanate groups with a mixture comprising:

(i) compounds which are reactive towards isocyanates and contain at least 5 ethylene oxide units and (ii) compounds which are reactive toward isocyanates and contain less than 5 ethylene oxide units.

2. A carbodiimide obtained according to a process as claimed in claim 1.

3. A carbodiimide mixture comprising compounds which contain ester structures and carbodiimides obtained according to a process as claimed in claim 1.

4. A mixture as claimed in claim 3 further comprising at least one compound selected from the following group:

polyurethanes containing ester structures, polycondensation products such as thermoplastic polyesters such as polyethylene terephthalate and polybutylene terephthalate, polyether esters, polyester esters, polyesteramides, polycaprolactones, unsaturated polyester resins and polyamides.

5. A mixture as claimed in claim 3 comprising carbodiimides as claimed in claim 1 in an amount of from 0.05 to 10% by weight, based on the total weight of the mixture.

6. A mixture as claimed in claim 4 comprising carbodiimides as claimed in claim 1 in an amount of from 0.05 to 10% by weight, based on the total weight of the mixture.

* * * * *